(12) United States Patent
Cho et al.

(10) Patent No.: US 9,273,321 B2
(45) Date of Patent: Mar. 1, 2016

(54) IN VITRO PLANT BIOASSAY METHODS

(71) Applicant: PIONEER HI BRED INTERNATIONAL INC, Johnston, IA (US)

(72) Inventors: Myeong-Je Cho, Santa Clara, CA (US); David C. Cerf, Palo Alto, CA (US); Deping Xu, Johnston, IA (US); Zuo-Yu Zhao, Johnston, IA (US)

(73) Assignee: PIONEER HI BRED INTERNATIONAL INC., Johnston, IA (US)

( * ) Notice: Subject to any disclaimer, the term of this patent is extended or adjusted under 35 U.S.C. 154(b) by 0 days.

(21) Appl. No.: 14/517,110

(22) Filed: Oct. 17, 2014

(65) Prior Publication Data
US 2015/0037807 A1   Feb. 5, 2015

Related U.S. Application Data

(63) Continuation of application No. 12/977,715, filed on Dec. 23, 2010, now abandoned.

(60) Provisional application No. 61/291,704, filed on Dec. 31, 2009.

(51) Int. Cl.
   C12N 15/82    (2006.01)
   A01G 1/00     (2006.01)
   G01N 33/50    (2006.01)

(52) U.S. Cl.
   CPC ............. *C12N 15/821* (2013.01); *A01G 1/001* (2013.01); *C12N 15/8201* (2013.01); *C12N 15/8227* (2013.01); *C12N 15/8286* (2013.01); *G01N 33/5097* (2013.01); *G01N 2333/415* (2013.01); *G01N 2333/43552* (2013.01)

(58) Field of Classification Search
   None
   See application file for complete search history.

(56) References Cited

U.S. PATENT DOCUMENTS

2006/0021087 A1   1/2006   Baum et al.
2008/0153102 A1   6/2008   Huang et al.

FOREIGN PATENT DOCUMENTS

| WO | 99/16890 A2 | 4/1999 |
|---|---|---|
| WO | 00/70066 A1 | 11/2000 |
| WO | 2006/066054 A2 | 6/2006 |
| WO | WO 2006066054 A2 * | 6/2006 |

OTHER PUBLICATIONS

De Maagd, et al, Trends Genet. (2001) 17: pp. 193-199.*
Marrone et al. (J. Econ. Entomol. 78: pp. 290-293 (1985)).*
Vaughn et al. (Crop Sci., pp. 931-938 (2005)).*
Meyers (1995), Molecular Biology and Biotechnology: A Comprehensive Desk Reference, Pesticide Producing Bacteria, p. 671, left col., second full paragraph.*
International Search Report and Written Opinion for International Application No. PCT/US2010/062018 dated Mar. 21, 2011.
Cho, et al., "Transformed $T_0$ orchardgrass (*Dactylis glomerata* L.) plants produced from highly regenerative tissues derived from mature seed," Plant Cell Reports, 2001, vol. 20, pp. 318-324.
Mahon et al., "Environmental stress and the efficacy of Bt cotton" The Australian Cotton Grower, pp. 18-22 (2002).
Vaughn et al., "A Method of Controlling Corn Rootworm Feeding Using a Bacillus thuringiensis Protein Expressed in Transgenic Maize" CropSci., pp. 931-938 (2005).
De Maagd, et al., "How Bacillus thuringiensis has evolved specific toxins to colonize the insect world" Trends Genet. 17 pp. 193-199(2001).
Gao, et al., "Fungal pathogen protection in potato by expression of a plant defensin peptide," Nature America Inc., Nature Biotechnology, pp. 1307-1310 (Dec. 18, 2000).
Radi, et al., "Expression of sarcotoxin IA gene via a root-specific tob promoter enhanced host resistance against parasitic weeds in tomato plants," Plant Cell Rep (2006) 25: 297-303.
Chan, et al., "Transgenic tomato plants expressing in Arabidopsis thionin (Thi2.1) driven by fruit-inactive promoter battle against phytopathogenic attack," Planta (2005) 221:386-293.

* cited by examiner

*Primary Examiner* — David T Fox
*Assistant Examiner* — Jared Shapiro

(57) ABSTRACT

The present invention provides assays and methods for efficiently testing a polynucleotide of interest for a phenotype in a root. In some embodiments, the assays and methods include regenerating green tissue that is transgenic for at least one polynucleotide of interest into one or more transgenic plantlets that have at least one transgenic root. Further provided are methods of making a root assay by contacting green tissue with a first rooting medium to produce a plantlet and a plurality of roots. Additionally provided are methods of assaying for insecticidal activity on a live root. Accordingly provided herein is a substantially contamination-free, root bioassay. Further provided are methods of identifying a promoter having activity in a root.

11 Claims, 1 Drawing Sheet

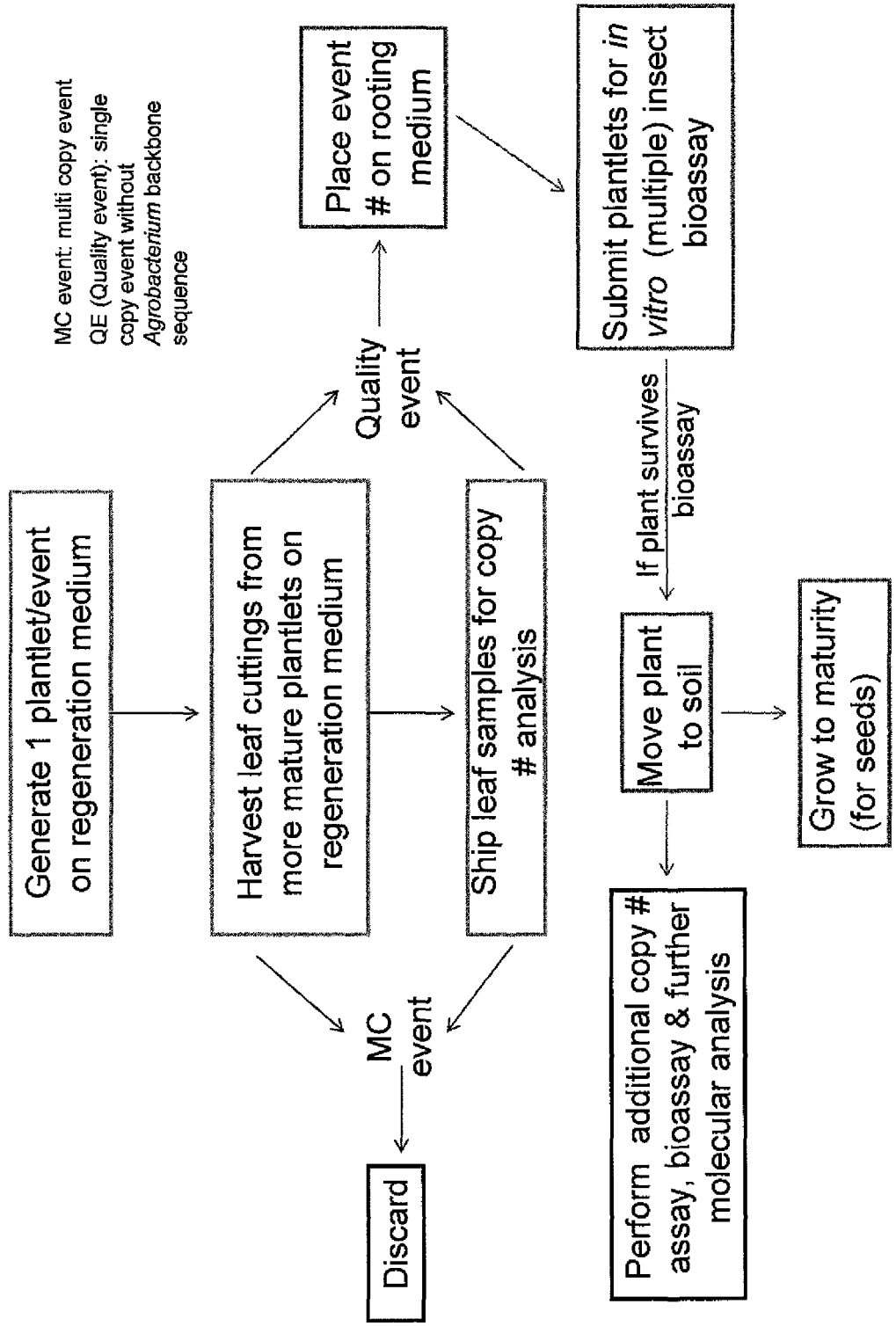

IN VITRO PLANT BIOASSAY METHODS

CROSS-REFERENCE TO RELATED APPLICATIONS

This application is a continuation of U.S. patent application Ser. No. 12/977,715, filed Dec. 23, 2010, which claims the benefit of U.S. Provisional Application No. 61/291,704, filed Dec. 31, 2009, which is herein incorporated by reference in its entirety.

FIELD OF THE INVENTION

The invention relates to the field of genetic manipulation of plants; in particular, the invention provides assays and methods for efficiently testing a polynucleotide of interest for a phenotype in a plant tissue such as a plantlet, a root or a leaf.

BACKGROUND OF THE INVENTION

The economic value of roots arise not only from harvested roots, but also from the ability of roots to alter the soil in which they grow and to funnel nutrients to support growth and increase vegetative material, seeds, fruits, etc.

Roots have four main functions. First, they anchor the plant in the soil. Second, they facilitate and regulate the molecular signals and molecular traffic between the plant, soil and soil fauna. Third, the root provides a plant with nutrients gained from the soil or growth medium. Fourth, they condition local soil chemical and physical properties. Roots arise from meristems cells that are protected by a root cap during root elongation, but as the root grows out, the cap cells abscise and the remaining cells differentiate to the tip. Depending on the plant species, some surface cells of roots can develop into root hairs. Some roots persist for the life of the plant, others gradually shorten as the ends slowly die back and some may cease to function altogether due to external influences.

Because plants are sessile organisms, their survival is critically dependent on rapid adaptation to environmental changes. In the soil, change can arise from alteration of the concentration of oxygen or carbon dioxide, nutrient availability, the presence (or absence) of microorganisms and overall soil humidity. For example, oxygen levels in the rhizosphere decrease rapidly during flooding. Hypoxic or anoxic conditions occur in submerged plant tissues and can have lasting effects on the subsequent growth and/or development of the plant.

Roots are also the sites of intense chemical and biological activities and as a result can strongly modify the soil they contact. For example, roots secrete a wide variety of high and low molecular weight molecules into the rhizosphere in response to biotic and abiotic stresses. They are also capable of absorbing toxic substances from the soil and then storing or modifying the toxins, resulting in soil improvement.

Roots coat themselves with surfactants and mucilage to facilitate these types of activities. Specifically, roots attract and interact with beneficial microfauna and flora that help to mitigate the effects of toxic chemicals, pathogens and stress in addition to facilitating water and nutrient assimilation and mobilization. Nutrients can take the form of ions and organic and inorganic compounds. Uptake of nutrients by roots produces a "source-sink" effect in a plant. The greater the source of nutrients, the larger "sinks" (such as stems, leaves, flowers, seeds, fruits, etc.) can grow.

Currently, transient gene expression has been applied to dicot species using the hairy root system to do a quick gene testing in roots, but establishing the hairy root system for maize and delivering transgenes in roots using *Agrobacterium rhizogenes* has been difficult. Generating transgenic maize plants with a callus tissue system by standard protocols uses a whole cycle of the transformation process which is a time-consuming process.

To date, there is only limited ability to efficiently and quickly test genes and root promoters in vivo in a root, for example, to assess the strength of a promoter in a root, to assess a gene's effect on the tolerance of roots to pests that attack roots (e.g., insects, fungi, bacteria, viruses, or nematodes) or to assess a gene's effect on the nutritional composition of roots for human food or animal feed applications. Thus a need exists for a highly efficient way to test polynucleotides in the root of a plant and generate plants expressing them in the root.

SUMMARY OF THE INVENTION

Compositions and methods are provided for efficiently testing a polynucleotide of interest for a phenotype in a plant tissue. While the invention is primarily discussed with respect to the root, it is recognized that the leaf, the plantlet, or other tissues may be used in the methods of the invention. More specifically, the embodiments of the present invention relate to assays and methods of regenerating green tissue into one or more plantlets that have at least one root. In some examples, the green tissue is transgenic for at least one polynucleotide of interest and the green tissue is regenerated into one or more transgenic plantlets having at least one transgenic root. The root, plantlet, or leaf, non-transgenic or transgenic, may be optionally subjected to a biotic stress, pest, or pathogen. The plant tissue may be assayed for one or more phenotypes. Such root phenotypes include but are not limited to increased root size, increased overall root mass, altered root architecture, increased expression level of mRNA or protein, increased biochemical content, increased tolerance or resistance to a pest or pathogen, modulation in biotic mass of the root, modulated yield, such as increased yield, as compared to the corresponding phenotype of a control. Similar phenotypes can be assessed for the leaf and plantlet.

Also provided herein are methods of making a root assay by contacting green tissue with a first rooting medium to produce a plantlet. The rooting medium may be a liquid, gel, or solid medium, including, for example, a medium gelled with agar or an agar substitute. The plantlet has at least one root that is removed from the medium and is contacted with a second rooting medium to produce a plurality of roots. In some embodiments, the rooting medium lacks agar or an agar substitute Additionally, a method of assaying for insecticidal activity on a live root is provided herein. The method includes regenerating green tissue into one or more plantlets comprising at least one live root. In some embodiments, the green tissue is transgenic for a polynucleotide of interest. The at least one root of the plantlet is contacted with a rooting medium. The root is exposed to one or more pests to infest the medium for infestation. In some embodiments, the medium and pest are substantially free of contamination. A phenotype of the root and/or pest is determined.

Accordingly, one of the embodiments includes a substantially contamination-free, root bioassay. The bioassay includes a live monocot plantlet with at least one live root. In some examples, the plantlet has at least one live root that is transgenic for a polynucleotide of interest. The root is placed in culture dish. The dish includes a rooting medium that contacts the root of the plantlet.

Methods of identifying a promoter having activity in plant tissue, particularly the root, are also provided. The methods relate to regenerating green tissue transgenic for a promoter of interest operably linked to a polynucleotide into one or more stably transformed transgenic plantlets. The plantlets have at least one live transgenic root. Further encompassed by the methods is determining whether the polynucleotide is expressed in root cells of the plantlet. The relative strength of a promoter in a root cell, the spatial expression of a promoter in the root, or whether the promoter is a root-preferred promoter may also be evaluated if desired. The methods may include determining the expression level of the polynucleotide and/or polypeptide encoded by the polynucleotide in root cells of the plantlet.

Other objects, features, advantages and aspects of the present invention will become apparent to those of skill from the following description.

BRIEF DESCRIPTION OF THE DRAWINGS

FIG. 1 shows a flow chart demonstrating an efficient screening scheme using in vitro bioassay plantlets.

DETAILED DESCRIPTION OF THE INVENTION

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

Indeed, the invention may be embodied in many different forms and should not be construed as limited to the embodiments set forth herein; rather, these embodiments are provided so that this disclosure will satisfy applicable legal requirements.

Many modifications and other embodiments of the invention set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. The articles "a" and "an" are used herein to refer to one or more than one (i.e., to at least one) of the grammatical object of the article. By way of example, "an element" means one or more than one element.

As used herein, the term "transgenic" means a plant or plant cell or plant part (e.g., a plant tissue or a plant organ) that comprises genetic material additional to the naturally occurring nucleic acid within the plant, cell or part. For example, the genome of a transgenic plant or plant cell or plant part may comprise nucleic acid from a different organism such as an animal, insect, bacterium, fungus or different plant species or variety. Alternatively, the genome of a transgenic plant or plant cell or plant part may comprise one or more additional copies of nucleic acid that occur naturally in the same plant species or variety. Alternatively, the genome of a transgenic plant or plant cell or plant part may comprise nucleic acid that does not occur in nature e.g., RNAi. The genome of a transgenic plant or plant cell or plant part may also contain a deletion relative to the genome of an isogenic or near-isogenic naturally-occurring plant e.g., as a result of homologous recombination or recombinase-induced recombination.

As used herein, the term "green tissue" refers to green regenerative tissue or green callus tissue which is green, shiny, nodular and compact as compared to monocot plant callus tissue. Green tissues are organogenic and have meristem-like structures. See U.S. Pat. No. 7,102,056, incorporated by reference in its entirety.

The term "root-preferred" is intended to mean that expression of the heterologous polynucleotide sequence is most abundant in the root. While some level of expression of the heterologous nucleotide sequence may occur in other plant tissue types, expression occurs most abundantly in a cell of the root or in a type of root, which may include, but is not limited to primary, lateral, and adventitious roots.

The term "root" is intended to mean any part of the root structure, including but not limited to, the root cap, apical meristem, protoderm, ground meristem, procambium, endodermis, cortex, vascular cortex, epidermis, and the like.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers.

Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters".

The term "dim light" refers to light that is approximately 5 to 50 $\mu E\ m^{-2}\ s^{-1}$.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) Meth. Enzymol. 143:277) and particle-accelerated or "gene gun" transformation technology (Klein et al. (1987) Nature (London) 327:70-73; U.S. Pat. No. 4,945, 050, incorporated herein by reference).

Previously a whole cycle of the transformation process was used to generate transgenic maize plants with a callus tissue system, but this is a time-consuming process. Transient gene expression has been applied to dicot species using the hairy root system to do a quick gene testing in roots, but establishing the hairy root system for maize and expressing transgenes using Agrobacterium rhizogenes have been difficult. The current invention utilizes a highly regenerative tissue system which can produce transgenic organogenic tissues ready for shoot regeneration and root formation. For example, using a visible marker, transgenic sectors can be easily identified under a fluorescence microscope and used for fast and continuous root production as well as shoot regeneration from transgenic green tissues by placing them directly on the rooting medium. Green tissues are more organogenic than callus tissues, and advantageously these green tissues can be maintained for long periods with a minimal loss of regenerability. This is in contrast to the rapid loss of regenerability that occurs when using a standard callus tissue system. A further advantage from practicing the methods and bioassays described herein is that, because green tissue is used, multiple plants can be produced from the same transgenic event during an extended time period.

Accordingly, provided herein are methods and assays for efficiently identifying the affects of expression of one or more polynucleotides of interest on plant tissues, particularly on the roots, transgenic for the one or more polynucleotides. The plant tissues are then analyzed for expression of the polynucleotides. Such affects or phenotypes for roots include, but are not limited to, modulated root size, overall root mass, root architecture, expression level of mRNA or protein, biochemical content of the root, tolerance to a biotic stress, tolerance or resistance to a pest, tolerance or resistance to a pathogen, yield, agronomic traits, increased disease resistance, nutritional enhancement, and the like. Also provided herein are methods and assays for efficiently determining whether a live plantlet or root has endogenous resistance or susceptibility to a biotic stress, such as a pest or pathogen. This would be of interest when screening germplasm using non-transgenic germinating plantlets/roots. In one example, polynucleotides effective for preventing corn root worm infestation or damage to roots associated with corn root worms may be identified using the provided methods and assays. In another aspect, the provided methods and assays may be used to determine whether a promoter is functional in a root cell, the relative strength of a promoter in a root cell, the spatial expression of a promoter in the root, or whether the promoter is a root-preferred promoter. In addition, the methods and assays described herein can be applied for rapid production of non-transgenic monocot plants or transgenic monocot plants. Efficient regeneration of plants would facilitate the study of plants with improved traits or phenotypes.

In one aspect, the methods include regenerating green tissue into one or more plantlets having at least one root. In some examples, the green tissue is transgenic for at least one polynucleotide of interest and gives rise to a transgenic plantlet having at least one transgenic root. In other applications, the green tissue can be used to produce root cultures, for example, transgenic root cultures. The polynucleotide of interest may be any suitable polynucleotide and may be either endogenous or heterologous to the plant cell being transformed. Polynucleotides encompass all forms of nucleic acid sequences including, but not limited to, single-stranded, double-stranded, triplexes, linear, circular, branched, hairpins, stem-loop structures, branched structures, and the like. In some instances, the polynucleotide of interest may encode a polypeptide of interest which is expressed in the cell. The polynucleotide of interest may confer a particular trait of interest to the plant, for example, such as, but not limited to disease resistant traits, insect resistant traits, nutritional enhancements, agronomic traits, firmness, acidity content, sugar content, texture, oil, starch, carbohydrate, or nutrient metabolism, increased oil production, increased protein production, unique oil and protein production, increased fermentable starch production, increased content of essential amino acids, increased content of fatty acids and the like. The polynucleotide of interest may be thioredoxin (Cho et al. 1999, Proc Natl Acad Sci USA 96: 14641-14646), lactoferrin, or lysozyme (Humphrey et al. 2002, J of Nutrition 32(6): 1214-1218). In one example, the polynucleotide of interest is a selectable or screenable marker gene. Exemplary marker genes are described elsewhere herein. In some instances, the polynucleotide of interest may suppress the expression of a target molecule in the plant cell, for example, $Ca^{2+}$-dependent protein kinase1 (CDPK1), Plant Cell 17:2911-2921 (2005); Arabidopsis Ran binding protein, AtRanBP1c, Plant Cell, 13: 2619-2630 (2001). The inhibitory polynucleotide may any suitable polynucleotide including but not limited to miRNA, a siRNA, dsRNA, an antisense polynucleotide and the like.

In one embodiment, recombinant vectors including one or more polynucleotides of interest suitable for the transformation of plant cells are prepared. These may be used to construct a recombinant expression cassette which can be introduced into the desired plant cell. In one example, an expression cassette will typically comprise a polynucleotide of interest operably linked to a promoter sequence and other transcriptional and translational initiation regulatory sequences which are sufficient to direct the transcription of the polynucleotide sequence in the intended tissues (e.g., entire plant, leaves, roots, etc.).

A number of promoters can be used in the practice of the present invention. The promoters can be selected based on the desired outcome. That is, the nucleic acids can be combined with constitutive, inducible, tissue-preferred, root-preferred promoters or other promoters for expression in the explant, green tissue, root, or regenerated plant.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313: 810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzene sulfonamide herbicide safeners; the maize GST promoter, which is activated by hydrophobic electrophilic compounds that are used as pre-emergent herbicides; and the tobacco PR-la promoter, which is activated by salicylic acid. Other chemical-regulated promoters of interest include steroid-responsive promoters. See, for example, the glucocorticoid-inducible promoter in Schena et al. (1991) Proc. Natl. Acad. Sci. USA 88:10421-10425 and McNellis et al. (1998) Plant J. 14(2):247-257 and the tetracycline-inducible and tetracycline-repressible promoters for example, Gatz et al. (1991) Mol. Gen. Genet. 227:229-237, and U.S. Pat. Nos. 5,814,618 and 5,789,156, herein incorporated by reference.

Root-preferred promoters are known and can be selected from the many available from the literature or isolated de novo from various compatible species. See, for example, Hire et al. (1992) Plant Mol. Biol. 20(2):207-218 (soybean root-specific glutamine synthetase gene); Keller et al. (1991) Plant Cell 3(10):1051-1061 (root-specific control element in the GRP 1.8 gene of French bean); Sanger et al. (1990) Plant Mol. Biol. 14(3):433-443 (root-specific promoter of the mannopine synthase (MAS) gene of *Agrobacterium tumefaciens*); and Miao et al. (1991) Plant Cell 3(1): 11-22 (full-length cDNA clone encoding cytosolic glutamine synthetase (GS), which is expressed in roots and root nodules of soybean). See also Bogusz et al. (1990) Plant Cell 2(7):633-641, which discloses two root-specific promoters isolated from hemoglobin genes from the nitrogen-fixing nonlegume *Parasponia andersonii* and the related non-nitrogen-fixing nonlegume Trema tomentosa. The promoters of these genes were linked to a beta-glucuronidase reporter gene and introduced into both the nonlegume *Nicotiana tabacum* and the legume *Lotus corniculatus*, and in both instances root-specific promoter activity was preserved. Leach et al. (1991) describe their analysis of the promoters of the highly expressed rolC and rolD root-inducing genes of *Agrobacterium rhizogenes* (see Plant Science (Limerick) 79(1):69-76). They concluded that enhancer and tissue-preferred DNA determinants are dissociated in those promoters. Teeri et al. (1989) EMBO J. 8(2):343-350 used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, which is an especially desirable combination of characteristics for use with an insecticidal or larvicidal gene. The TR1' gene, fused to nptII (neomycin phosphotransferase II), showed similar characteristics. Additional root-preferred promoters include the VfENOD-GRP3 gene promoter (Kuster et al. (1995) Plant Mol. Biol. 29(4): 759-772); the ZRP2 promoter (U.S. Pat. No. 5,633,636); the IFS1 promoter (U.S. patent application Ser. No. 10/104,706) and the rolB promoter (Capana et al. (1994) Plant Mol. Biol. 25(4):681-691). See also U.S. Pat. Nos. 5,837,876; 5,750, 386; 5,459,252; 5,401,836; 5,110,732; and 5,023,179.

A strongly or weakly constitutive plant promoter that directs expression of a polynucleotide of interest nucleic acid in all tissues of a plant can be employed. Such promoters are active under most environmental conditions and states of development or cell differentiation. In addition to the promoters mentioned above examples of constitutive promoters include the 1'- or 2'-promoter of *Agrobacterium tumefaciens*, and other transcription initiation regions from various plant genes known to those of skill. Where over expression of a polypeptide of interest is detrimental to the plant, one of skill will recognize that weak constitutive promoters can be used for low-levels of expression. Generally, by "weak promoter" a promoter that drives expression of a coding sequence at a low level is intended. By "low level" levels from about {fraction (1/1000)} transcripts to about {fraction (1/100,000)} transcripts, to about as low as {fraction (1/500,000)} transcripts per cell are intended. Alternatively, it is recognized that weak promoters also include promoters that are expressed in only a few cells and not in others to give a total low level of expression. Where a promoter is expressed at unacceptably high levels, portions of the promoter sequence can be deleted or modified to decrease expression levels. In those cases where high levels of expression is not harmful to the plant, a strong promoter, e.g., a t-RNA, or other pol III promoter, or a strong pol II promoter, e.g., the cauliflower mosaic virus promoter, CaMV, 35S promoter can be used.

Alternatively, a plant promoter can be under environmental control. Such promoters are referred to as "inducible" promoters. Examples of environmental conditions that may alter transcription by inducible promoters include pathogen attack, anaerobic conditions, or the presence of light. In some cases, it is desirable to use promoters that are "tissue-specific" and/ or are under developmental control such that the polynucleotide of interest is expressed only in certain tissues or stages of development, e.g., leaves, roots, shoots, etc. Promoters of genes related to pesticide resistance and related phenotypes may also be used.

Tissue specific promoters can also be used to direct expression of heterologous structural genes, including polynucleotides of interest. Thus, the promoters can be used in recombinant expression cassettes to drive expression of any gene whose expression is desirable in the transgenic plantlets. Similarly, enhancer elements, e.g., derived from the 5' regulatory sequences or intron of a heterologous gene, can also be used to improve expression of a heterologous structural gene.

In general, the particular promoter used in the expression cassette in plants depends on the intended application. Any of a number of promoters which direct transcription in plant cells can be suitable. In addition to the promoters noted above, promoters of bacterial origin which operate in plants include the octopine synthase promoter, the nopaline synthase promoter and other promoters derived from T1 plasmids. See, Herrera-Estrella et al. (1983) Nature 303:209. Viral promoters include the .sup.35S and 19S RNA promoters of CaMV. See, Odell et al. (1985) Nature 313:810. Other plant promoters include the ribulose-1,3-bisphospha-the carboxylase small subunit promoter and the phaseolin promoter. The promoter sequence from the E8 gene (see, Deikman and Fischer (1988) EMBO J. 7:3315) and other genes are also favorably used. Promoters specific for monocotyledonous species are also considered (McElroy and Brettell (1994) "Foreign gene expression in transgenic cereals" Trends Biotech. 12:62-68.) Alternatively, novel promoters with useful characteristics can be identified from any viral, bacterial, or plant source by methods, including sequence analysis, enhancer or promoter trapping, and the like, known in the art.

In preparing expression vectors, sequences other than the native promoter of the polynucleotide of interest may also be used. If proper polypeptide expression is desired, a polyadenylation region can be derived from the native gene, from a variety of other plant genes, or from T-DNA. Signal/localization peptides, which, e.g., facilitate translocation of the expressed polypeptide to internal organelles (e.g., chloroplasts) or extracellular secretion, can also be employed.

The vector can include a selectable or screenable marker gene as, or in addition to, a particular polynucleotide of interest to provide or enhance the ability to identify transformants by conferring a selectable phenotype on the transformed plant cells. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening", e.g., bar, pat, GAT, PMI, hpt, nptII, DS-RED, GFP, YFP, GUS. Of course, many examples of suitable marker genes are known to the art and can be employed in the methods and assays. Marker genes may also be used to monitor gene expression and protein localization in plant cells, such as root cells via visualizable reaction products or by direct visualization of the gene product itself. Accordingly, many selectable marker coding regions may be used in connection with a promoter. Examples of selectable markers include nptII. (Potrykus et al., 1985), which provides kanamycin resistance and can be selected for using kanamycin, G418, paromomycin, etc.; bar, which confers bialaphos or phosphinothricin resistance; a nitrilase such as bxn from *Klebsiella ozaenae* which confers resistance to bromoxynil (Stalker et al., 1988) and a mutant acetolactate synthase (ALS) which confers resistance to imidazolinone, sulfonylurea or other ALS inhibiting chemicals (European Patent Application 154,204, 1985) and a methotrexate resistant DHFR (Thillet et al., 1988). Such vectors also generally include one or more dominant selectable marker genes, including genes encoding antibiotic resistance (e.g., resistance to hygromycin, kanamycin, bleomycin, G418, streptomycin, paromomycin, or spectinomycin) and herbicide-resistance genes (e.g., resistance to phosphinothricin acetyltransferase or glyphosate) to facilitate manipulation in bacterial systems and to select for transformed plant cells.

A number of techniques and protocols may be used to produce green tissue. For example, when it is desired that green tissue be transgenic for a polynucleotide of interest, the green tissue itself may be transformed using conventional methods, for example, particle bombardment or *Agrobacterium*. See Example 1. Alternately, green tissue can be made transgenic for a polynucleotide of interest by transforming an explant that can give rise to green tissue when the explant is cultured for a time and under conditions sufficient for the initiation and growth of green tissue to occur. As described, green tissue induction is carried out under dim light. The length of exposure of the plant cells to dim conditions may vary based in part on the type of plant species and genotype being transformed.

Any suitable explant that can give rise to green tissue may be used in the methods described herein. The explant can be from a monocot. It will be understood by one skilled in the art that the explant may comprise a plant cell, a tissue or an organ. Exemplary explants for use with the methods include but are not limited to embryos, green tissue, callus such as Type I or II, cell suspensions, cotyledons, including scutella, meristems, seedlings, mature and immature seeds, leaves, stems, shoots, scutella, nodes, leaf bases, or roots. See U.S. patent application publication no. 20080280361, U.S. Pat. Nos. 5,569,834; 5,416,011; 5,824,877; 7,064,248. When the explant is an embryo from a maize plant, the method may include pollinating ears from the treated maize plant, harvesting the ears so that the ears or embryos may be prepared for transformation. See, for example, Green and Phillips (Crop Sci. 15:417-421, 1976). Maize immature embryos can be isolated from pollinated plants, as another example, using the methods of Neuffer et al. ("Growing Maize for genetic purposes." In: Maize for Biological Research W. F. Sheridan, Ed., University Press, University of North Dakota, Grand Forks, N. Dak. 1982.). The explant may be prepared using any suitable technique and may include, for example, isolating the explant from the plant, excising plant cell, tissue, or organ from the explant, sterilizing the plant cell, tissue, organ, or explant or combinations thereof. In some cases, the explant is an embryo, such as an immature embryo from a monocot such as corn. In one example, the methods include transforming one or more immature embryos from the monocot using conventional methods such as *Agrobacterium*-mediated transformation or particle bombardment. See Example 1. As described, green tissue induction is carried out under dim light for a length of time sufficient for the initiation and growth of green tissue to occur. The length of exposure of the plant cells to dim conditions may vary based in part on the type of plant species and genotype being transformed.

In cases where the explant is other than green tissue, the explant can be used to generate green tissue using commonly known techniques. For example, green tissue can be obtained by culturing immature embryos under appropriate conditions to initiate the formation of green tissue. See, for example, U.S. Pat. Nos. 6,541,257, 6,235,529, 7,102,056. When *Agrobacterium* is used to transform cells of the explant to generate transgenic green tissue, typically the explant such as immature embryos are co-cultivated for about 1-3 days in the dark and rested for an additional 1-3 days in resting medium, typically without selection. The explant is contacted with green tissue induction medium under dim light to produce green tissue. The green tissue induction medium may optionally contain a selective agent, e.g. bialaphos and carbinicellin, when producing transgenic green tissue. Usually, the green tissue-induction media used in the methods contains different combinations of an auxin, cytokinin, and copper in amounts effective to initiate the formation of green tissue. In one example of green tissue-induction medium the auxin is 2,4-dichlorophenoxyacetic acid (2,4-D), the cytokinin is 6-benzylaminopurine (BAP) and copper is $CuSO_4$. This culturing step usually takes about 2-3 weeks, preferably at about 24° C.-28° C. under dim light.

In some circumstances, it may be desirable to break the green tissue into one or more pieces to facilitate proliferation and more stringent selection. The method may also include subculturing the broken pieces of green tissue in the presence of the selection agent for about 2-3 weeks. About 3 to 5 rounds of subculturing with a selective agent is typically considered sufficient to select for transformed tissue.

Transgenic green tissue can also be obtained by bombarding immature embryos and culturing them under appropriate conditions to initiate the formation of green tissue. Immature embryos are isolated using any suitable technique and placed scutellum-side up in an osmotic medium. The embryos are bombarded with solid particles, such as gold particles, coated with the polynucleotide of interest. The embryos are contacted with green tissue induction medium that typically lacks a selective agent and cultured under dim light for about 3-7 days, usually at about 24° C.-28° C. to produce transgenic green tissue. In some circumstances, it may be desirable to break the green tissue into one or more pieces to facilitate proliferation and more stringent selection. The method may also include subculturing the broken pieces of green tissue in the presence of the selection agent for about 2-3 weeks. About 3 to 5 rounds of subculturing with a selective agent is typically considered sufficient to select for transformed tissue. Optionally, the putative transgenic tissues are maintained and proliferated on green tissue induction or maintenance medium containing a selective agent. Once a sufficient amount of green tissues are obtained, the green tissue may be plated on solid regeneration/rooting medium optionally containing a selective agent and exposed to a higher light intensity, approximately 45 to 100 µE m$^{-2}$ s$^{-1}$, on a 16-h light cycle. After about 4 to 6 weeks, regenerated plantlets may be transferred to soil.

When green tissues are used as targets for bombardment, the green tissue may be pretreated with an osmotic solution. See Example 1. After about 4 hours, the green tissue is bombarded using any suitable particle. One transformed, transgenic green tissues are selected and cultured in a similar manner as that used for green tissue obtained by particle bombardment of immature embryos. See Example 1.

Transgenic regions of the green tissue obtained by any method may be confirmed or identified using any suitable gene such as a maker gene. For convenience, visible marker genes such as RFP, GFP, EGFP, lucieferase or YFP are normally utilized to identify transgenic regions in the green tissue using standard techniques and instruments such as a fluorescence microscope. The transgenic regions of the green tissue may be isolated by cutting the transgenic regions from the non-transgenic regions of the green tissue. The transgenic regions are typically cut into several pieces and placed on maintenance medium for further proliferation. In some examples, the non-transgenic green tissue may be cut into several pieces and placed on maintenance medium for further proliferation. In some cases, the maintenance medium and green tissue initiation medium are the same.

The green tissues are transferred directly onto rooting medium so that one or more roots are produced. Any suitable rooting medium may be used, including but not limited to phytohormone-free medium. For example, MS basal medium supplemented with IBA (e.g., 0.5 mg/L) can be used to induce root formation, if necessary. Depending upon the genotype, different levels of an auxin and cytokinin (i e, a different auxin/cytokinin ratio) provide optimal results. The medium may be of any suitable form such as solid, liquid or gel, for example, medium gelled with agar or an agar substitute gelling agent such as PHYTAGEL™ (Sigma-Aldrich, St. Louis, Mo., USA). Normally, when the green tissue is transgenic the rooting medium contains a selective agent or one is added to the medium. The green tissue is contacted with rooting medium that induces root formation for a time and under conditions sufficient to initiate root growth from the green tissue, thereby producing a plantlet.

If desired, the green tissue may be incubated on regeneration medium prior to placing tissues on rooting medium. Any suitable regeneration medium can be used including without limitation to phytohormone-free medium and others. One skilled in the art will be familiar with such media. Exposing the green tissue to regeneration medium can facilitate more efficient root production. The length of incubation is often for a short period of time such as 1-3 weeks.

In one embodiment, the methods of the invention may use plant tissues selected from, but not limited to, whole plantlets, plantlet parts, plantlet leaves or plantlet roots.

The following discussion is directed to assay of roots but can be adapted for the assay of other plant tissues including plantlets and leaves. Roots can be produced with shoot regeneration or without any shoot regeneration. If shoot regeneration is desired, the green tissue is contacted with shoot regeneration medium for a sufficient length of time and under conditions to generate shoots. In some instances, the green tissue may be contacted with shoot regeneration medium prior to, concurrent with, or subsequent to contacting the green tissue with rooting medium in order to produce a plantlet.

Plantlets having one or more roots may be removed from the solidified agar medium and the agar rinsed off the roots. In one aspect, the roots are placed onto suitable assay dishes or containers such as a culture dish, e.g. Phyta trays or Petri dishes.

When doing so, it may prove advantageous to continue to keep the roots growing and alive to more closely mimic real life infestations, infections or stresses of plants. Accordingly, the roots are placed in a rooting medium such as MSA and MSB in the culture dish so that root production is continuous. Typically, MSA includes MS salts and vitamins, 2% sucrose, 0.35% Phytagel and 3 mg/L bialaphos and MSB includes MS salts and vitamins, 2% sucrose, 0.25% Phytagel, 0.5 mg/L IBA and 3 mg/L bialaphos. Additional exemplary rooting media are described above and in the Examples herein. In some examples, the rooting medium lacks agar or an agar-substitute.

In another aspect, steps are taken to prevent or inhibit the growth of unwanted contaminants e.g. microbes, such as bacteria, mold, or fungi in the assay. For example, a biocide such as Plant Preservative Mixture (PPM—0.1350% 5-chloro-2methyl-3(2H)-isothiazolone, 0.0412% 2-methly-3 (2H)-isothiasolone, 99.8238% inert ingredients, Plant Cell Biotechnology, Inc., Washington, D.C.) may be added to the rooting medium to prevent or inhibit fungal and bacterial development. Additionally, the dish may be sterile or substantially sterile. Further, the use of sterile filter papers rather than agar in the dish can be used to facilitate the transfer of rooting solution to plant roots and reduce fungal and bacterial development. Any means, technique or object, such as filter paper, that facilitates the contact between the rooting medium and roots may be used so long as it does not break off or kill the roots. Contact between the medium and the roots may be facilitated by placing an object on top of the roots to force the roots downward into the dish. The object may be a screen or grid.

Use of the methods and assays described herein serve as an efficient means for testing endogenous genes or a polynucleotide of interest for various phenotypes in non-transgenic roots or roots transgenic for the polynucleotide respectively. As described elsewhere herein, the polynucleotide may be any suitable polynucleotide. Polynucleotides suitable for use in the methods and assays described herein may be either endogenous or heterologous to the plant cell of the explant to be transformed. The polynucleotide may be RNA, DNA or both. Polynucleotides encompass all forms of nucleic acid sequences including, but not limited to, single-stranded, double-stranded, triplexes, linear, circular, branched, hairpins, stem-loop structures, branched structures, and the like. The polynucleotide may be a ds RNA molecule, such as a dsRNA molecule that upon consumption by a pest decreases pest infestation. See U.S. Publication No. 20060021087. In some instances, the polynucleotide of interest may encode a polypeptide of interest which is already expressed in the native root cell. The polynucleotide of interest may confer or modulate one or more particular phenotypes of interest to the root, for example, such as, but not limited to increased root size, increased overall root mass, altered root architecture, increased expression level of mRNA or protein, increased biochemical content, increased tolerance to stress, increased tolerance or resistance to a pest, increased tolerance or resistance to a pathogen, increased yield desirable agronomic traits, increased disease resistance, nutritional enhancements, and the like. As will be appreciated by one skilled in the art, there may be overlap or correlations between the observed phenotypes.

Exemplary promoters to drive expression of the polynucleotide of interest include without limitation constitutive, inducible, or root-preferred promoters and are described elsewhere herein and can be selected from the many available from the literature. Known or novel promoters may be tested for functionality in a root cell, the relative strength of the promoter in a root cell, the spatial expression of the promoter in the root, or whether the promoter is a root-preferred promoter using the methods and assays described herein.

The plant tissue is evaluated for expression levels of endogenous polynucleotides of interest or heterologous polynucleotides of interest. Expression at the RNA level can be determined to identify and/or quantitate expression of a polynucleotide of interest. Standard techniques for RNA analysis can be employed and include PCR amplification assays using oligonucleotides primers designed to amplify only the heterologous RNA templates and solution hybridization assays using heterologous nucleic acid-specific probes. The transgenic tissue may be evaluated for the polynucleotide of interest's impact on resistance to diseases, pests, pathogens, stresses, nutrients, or chemicals and the like. The chemical may be a pesticide or bactericide and the like.

Roots may be evaluated for expression levels of endogenous polynucleotides of interest or heterologous polynucleotides of interest, for example, in a transgenic root. Expression in the roots at the RNA level can be determined to identify and/or quantitative expression for a polynucleotide of interest. When the polynucleotide of interest is a root-preferred promoter, as will be understood by one skilled in the art, the transgenic root may be evaluated for expression of the polynucleotide operably linked to the root-preferred promoter. Standard techniques for RNA analysis can be employed and include PCR amplification assays using oligonucleotides primers designed to amplify only the heterologous RNA templates and solution hybridization assays using heterologous nucleic acid-specific probes. If desired, the roots can be analyzed for protein expression by fluorescent microscopy, FACS, or Western immunoblot analysis using the specifically reactive cognate antibodies. In addition, in situ hybridization and immunocytochemistry according to standard protocols can be done using heterologous nucleic acid specific polynucleotide probes and antibodies, respectively, to localize sites of expression within transgenic root tissue. Generally, a number of transgenic roots are usually screened for the polynucleotide of interest to identify and select plantlets with the most appropriate expression profiles, for example, in some examples, those that comparatively express the polynucleotide at the highest level or as compared to a control null for the polynucleotide of interest. In some cases, it may be desirable to have low levels of expression of an endogenous gene in the root.

Roots, such as roots transgenic for the polynucleotide of interest, may be evaluated for root size. Root size includes but is not limited to root biomass, root strength, root thickness, the formation of aerial roots, the number of aerial roots, length of roots, and the number of lateral and/or adventitious roots and the like and combinations thereof as compared as to a control. See U.S. Pat. No. 7,259,296. In one aspect, expression of the polynucleotide of interest increases root biomass, produces thicker roots, produces stronger roots, increases the formation of aerial roots, increases the number of aerial roots, increases the length of roots, and increases the number of lateral and/or adventitious roots or combinations thereof.

In another aspect, the roots may be evaluated for the endogenous or heterologous polynucleotide of interest's impact on root architecture. Aspects of root architecture that may be evaluated include without limitation root depth, root angle, root branching, number of root tips, nodal root diameter, nodal root volume, and root metabolic activity and the like or combinations thereof. See U.S. Pat. No. 7,557,266. One skilled in the art will be familiar with techniques for determining such aspects.

Expression of the endogenous or heterologous polynucleotide of interest may also affect the biochemical content of the root. See, for example, J. Exp. Bot. (2003) 54: 203-211 describing the effect of pmt gene overexpression on tropane alkaloid production in transformed root cultures of *Datura metel* and *Hyoscyamus muticus*.

The transgenic roots may be evaluated for the polynucleotide of interest's impact on resistance to diseases, pests, pathogens, stresses, nutrients, or chemicals and the like. The chemical may be a pesticide or bactericide and the like.

Accordingly, the embodiments encompass methods that are directed to protecting plants against root pathogens or biotic stresses such as fungal pathogens, bacteria, viruses, nematodes, pests, and the like. By "disease resistance" or "insect resistance" is intended that the plants avoid the harmful symptoms that are the outcome of the plant-pathogen interactions. U.S. Pat. No. 7,456,334. Pathogens of the embodiments include, but are not limited to, viruses or viroids, bacteria, insects, nematodes, fungi, and the like. Viruses include tobacco or cucumber mosaic virus, ringspot virus, necrosis virus, maize dwarf mosaic virus, etc. Nematodes include parasitic nematodes such as root knot, cyst, and lesion nematodes, etc. As described elsewhere herein, various changes in phenotype may be determined in the plantlet root, e.g. altering a plant's pathogen or insect defense mechanism or increasing the plant's tolerance to herbicides Advantageously, the present methods and assays use an intact, live root that takes place in a dish and allows for the continuous generation of plants from roots obtained from the green tissue. With respect to the continuous generation of transgenic plants from transgenic green tissue, advantageously these may be obtained from the same transgenic event. This is in contrast to other rootworm bioassay techniques that employ ground-up transformed roots or use seedlings in soil which are infested with either eggs or neonates. The former destroys the plant and requires new plants to be recreated with the same genomic character. The latter requires an assay of at least 14 days of duration and is often destructive in nature. It is challenging to determine the activity of the plant on the larvae as it is difficult to find the larvae in the soil. Advantageously, the status of the pests and root are easily observable using the assays and methods described herein since they do not require that the roots be immersed or buried in soil.

The assays and methods described herein are also economical from a time and space standpoint as they have a duration of about 1 to 14 days or less and extensive greenhouse space is not needed to perform the methods and assays, rather they can be performed in an incubator with lights. In one embodiment of the invention, the effect of insect application on plantlet, root or leaf damage may be assayed within about 1, 2, 3, 4, 5, 6, 7, 8, 9, 10, 11, 12, 13, 14 or more days after infestation with one or more pests.

Pests that may be used in the methods and assays include without limitation those insects belonging to the order of Lepidoptera, which would feed on the stalk and leaves, e.g.

European corn borer (*Ostrinia nubilalis*), Corn earworm (*Helicoverpa zea*), Fall armyworm (*Spodoptera frugiperda*), Western bean cutworm (*Richia albicosta*), Black cutworm (*Agrotis ipsilon*), Lesser cornstalk borer (*Elasmopalpus lignosellus*), Southwest corn borer (*Diatraea grandiosella*), Sugarcane borer (*Diatraea saccharalis*), Homoptera, e.g. Aphid (leaf feeding and root feeding), Leafhoppers, Coleoptera, e.g. Corn rootworms, Wireworms, or White grubs (Scarabs) or Heteroptera. In another aspect, steps are taken to prevent or inhibit the growth of unwanted contaminants e.g. microbes, such as bacteria, mold, or fungi in the assay. For example, a biocide such as PPM may be added to the medium to prevent or inhibit fungal and bacterial development. Further, the use of an absorbent material such as filter papers, rather than agar, in the Phytatray or Petri dish can be used to facilitate the transfer of nutrient solution to plant roots, while reducing fungal and bacterial development. If further contact is desired between the medium and the roots, a wire grid or screen may be placed on top of the roots.

Pests may be sterilized prior to contact with the root. In some examples, the eggs, larvae, instars or adults of the pests are treated to remove or kill bacterial or fungal spores which may include washing with once or multiple times with a solution such as ethanol or CHLOROX® bleach (The Chlorox company, Oakland, Calif.). The pests may be feed prior to infesting the roots. For example, neonates may be placed on artificial diet for 24 hours prior to being placed on the test roots. This eliminates any larvae that will have died in the initial 24 hours as well as allowing for the selection of uniform-sized and healthy test subjects. Allowing the neonates to feed for 24 hours provides the further benefit of causing the evacuation of any fungal or bacterial spores in the gut with the elimination of frass. In another aspect, the pest in any developmental stage such as eggs, larvae, instars, or adults may be sprayed with LYSOL® disinfectnant, e.g. EPA Reg No 777-72, in particular Professional LYSOL® disinfectant spray, EPA Reg No 777-72-625, or another disinfectant prior to infestation to help kill fungi and bacteria (LYSOL® disinfectnant Reckitt Benckiser Inc, Parsippany, N.J.).

Subsequent to pest infestation or exposure to the stress or pathogen, the root is incubated under appropriate conditions, for example, incubating the dish plus roots and pests at about 24° C.-28° C. under light or dark conditions. The roots may be subjected to pests of the appropriate developmental stage, for example, larvae, and appropriate number. Generally the duration of the assay is about 4-14 days. The phenotypes of the roots or pests or both may be observed at any suitable time point but are typically performed at completion. As understood by one skilled in the art, the damage to roots and pests can be determined in various ways, including objective and subjective techniques. For example, the roots may be scored for their damage by the pests on a scale of 0 to 5 with 0 indicating little or no observable damage to severe root damage. In addition, leaf damage can also be scored for direct feeding by the insects, or by color changes and wilting due to damage to the roots or stem. In some instances, color change in various plantlet parts, such as the leaves, stems, and/or roots, may be observed as a result of pest damage. Color change may occur in none, some or all of these parts. Pests may be scored to count "live" versus "dead" or "stunted" larvae and tabulating the results to express as a percentage of mortality. Any result of dead or stunted or combinations thereof over 50% is considered a positive result. In another aspect, the roots may be evaluated for resistance to any rootworm, for example, resistance to Southern corn rootworm (*Diabrotica undecimpuncata*), Western corn rootworm (*Diabrotica virgifera*), and/or Northern corn rootworm (*Diabrotica barber*), and the like. In some cases, the transgenic roots may be evaluated for the polynucleotide of interest's impact on resistance to a pest, such as any rootworm.

As another example, the plantlet may be scored for damage by the pests by observing the color change of the stem area above the crown of the roots. With respect to a normal plantlet of maize exposed to a pest, when the stem area above the crown darkens from pest damage, e.g. from WCRW damage; this color change indicates that the polynucleotide of interest is not effective for controlling pest infestation and/or damage to the stem. However, when little or no color change of the stem area above the crown is observed when the plantlet is exposed to a pest, this indicates that the polynucleotide of interest is effective for controlling pest infestations and/or damage to the plantlet. As another example, the crown of the plantlet may be scored for damage by the pests by determining the existence of holes in the crown. The number of holes in the crown can be translated into a numerical value which can be used to determine the overall activity of the polynucleotide of interest in protecting the plantlet.

Transgenic plants may be regenerated from green tissue that has a root testing positive for a desirable phenotype. A plant having the desired phenotype may be produced by regenerating the plant from the green tissue and the resultant plant entered into a plant breeding program. After 3-4 weeks, the regenerated transgenic plantlets may be transferred to soil and grown into a transgenic plant in a greenhouse. Accordingly, in one aspect, the methods may include growing the transgenic plantlet into a transgenic plant. Transgenic seed may also be obtained from the plant if desired.

Any well-known regeneration medium may be used for the practice of the provided methods. "Regeneration medium" (RM) promotes differentiation of totipotent plant tissues into shoots, roots, and other organized structures and eventually into plantlets that can be transferred to soil. Auxin levels in regeneration medium are reduced relative to MPM or, preferably, auxins are eliminated. It is also preferable that copper levels are reduced, e.g., to levels common in basal plant culture media such as MS medium. It is preferable to include a cytokinin in RM, as cytokinins have been found to promote regenerability of the transformed tissue. However, regeneration can occur without a cytokinin in the medium. Typically, cytokinin levels in RM are from about 0 mg/L to about 4 mg/L. RM also preferably includes a carbon source, preferably about 20 g/L to about 30 g/L, e.g., either sucrose or maltose.

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of interest. For transformation and regeneration of maize see, Gordon-Kamm, et al., (1990) The Plant Cell 2:603-618.

Regeneration can also be obtained from explants, green tissue, roots, plantlets, or parts thereof. Such regeneration techniques are described generally in Klee, et al., (1987) Ann. Rev. of Plant Phys. 38:467-486. The regeneration of plants from either single plant protoplasts or various explants is well known in the art. See, for example, Methods for Plant Molecular Biology, Weissbach and Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, The Maize Handbook, Freeling and Walbot, Eds., Springer, New York (1994); Corn and Corn Improvement, 3.sup.rd edition, Sprague and Dudley Eds., American Society of Agronomy, Madison, Wis. (1988).

Plants to be transferred to the growth chamber are removed from sterile containers and the solidified agar medium is rinsed off the roots. The plantlets are placed in a commercial potting mix in a growth chamber equipped with a misting device which maintains the relative humidity near 100% without excessively wetting the plant roots. Approximately three to four weeks are required in the misting chamber before the plants are robust enough for transplantation into pots or into field conditions. At this point, many plantlets, especially those regenerated from short-term callus cultures will grow at a rate and to a size similar to seed-derived plants. Plants regenerated from long-term callus, from suspension cultures, and from in vitro-selected callus will sometimes show phenotypic abnormalities, such as reduced plant size, leaf striping and delayed maturation. Care must be taken to assure controlled pollination with such plants. Ten to fourteen days after pollination, the plants are checked for seed set. If there is seed, the plants are then placed in a holding area in the greenhouse to mature and dry down. Harvesting is typically performed six to eight weeks after pollination.

One of skill will recognize that after the recombinant expression cassette comprising the polynucleotide of interest is stably incorporated in transgenic plants and confirmed to be operable, it can be introduced into other plants by sexual crossing. Any of a number of standard breeding techniques can be used, depending upon the species to be crossed.

This invention can be better understood by reference to the following non-limiting examples. It will be appreciated by those skilled in the art that other embodiments of the invention may be practiced without departing from the spirit and the scope of the invention as herein disclosed and claimed.

EXAMPLES

The present invention is further defined in the following Examples, in which parts and percentages are by weight and degrees are Celsius, unless otherwise stated. The disclosure of each reference set forth herein is incorporated herein by reference in its entirety.

Example 1

Production of Transgenic Maize Events Via Bombardment

Immature Embryos as a Bombardment Target

Ears of a maize (Zea mays L.) cultivar, PHR03, were surface-sterilized for 15-20 min in 20% (v/v) bleach (5.25% sodium hypochlorite) plus 1 drop of Tween 20 followed by 3 washes in sterile water. Immature embryos (IEs), typically 9 to 12 days after pollination, were isolated from ears and were placed scutellum-side up in an osmotic medium containing equimolar amounts of mannitol and sorbitol to give a final concentration of 0.4 M. The embryos were bombarded with gold particles coated with DNA containing bar/moPAT or another selectable marker using a PDS-1000 He biolistic device (Bio-Rad, Inc., Hercules, Calif.) at 650-1300 psi. Between 16 hr and 18 hr after bombardment, the bombarded embryos were placed on green tissue induction medium without osmoticum and grown at 26° C.±2° C. under dim light (10-50 uE m$^{-2}$ s$^{-1}$). Following the initial 4 to 10 day culturing period, each green tissue was broken into 1 to 3 pieces depending on tissue size and transferred to green tissue induction medium supplemented with bialaphos or another selective agent. Three weeks after the first round of selection, cultures were transferred to fresh green tissue induction medium containing a selective agent at 3 to 4 week intervals. Following identification of sufficient sized green, regenerative structures, tissues were then transferred directly onto 2 different shoot and root regeneration culturing schemes: (1) 7-14 days of incubation on 289 F shoot regeneration medium prior to placing tissues on rooting medium and (2) directly onto rooting medium. Two rooting media were also tested: (1) MSA containing MS salts and vitamins, 2% sucrose, 0.35% Phytagel and 3 mg/L bialaphos and (2) MSB containing MS salts and vitamins, 2% sucrose, 0.25% Phytagel, 0.5 mg/L IBA and 3 mg/L bialaphos. MSB was more efficient in root formation than MSA.

Green Tissues as a Bombardment Target

Ears of PHR03 were surface-sterilized as described above. Green tissues were induced and proliferated by culturing IEs on green tissue induction medium and used for bombardment. Green tissues, approximately two to three months old, were used as targets for bombardment. Tissues (4 to 6 mm) were transferred for osmotic pretreatment to green tissue induction medium containing 0.2 M mannitol and 0.2 M sorbitol. After 4 hr, tissues were bombarded as described above. Sixteen to 18 hr after bombardment, the bombarded tissues were placed on green tissue induction medium without osmoticum and grown at 26° C.±2° C. under dim light (10-50 uE m$^{-2}$ s$^{-1}$). Following the initial 4 to 10 day culturing period, each green tissue was broken into 1 to 3 pieces depending on tissue size and transferred to green tissue induction medium supplemented with bialaphos or another selective agent. Three weeks after the first round of selection, cultures were transferred to fresh green tissue induction medium containing a selective agent at 3 to 4 week intervals. Once transformed, transgenic green tissues are selected and cultured in a similar manner as that used for green tissue obtained by particle bombardment of immature embryos.

Example 2

Production of Transgenic Maize Events Via Agrobacterium

Preparation of Agrobacterium Suspension:

Agrobacterium tumefaciens harboring a binary vector containing DS-RED (RFP) reporter gene and a selectable marker (moPA 7) with or without a Bt gene was streaked out from a −80° frozen aliquot onto solid PHI-L medium and cultured at 28° C. in the dark for 2-3 days. PHI-L media comprised 25 ml/L stock solution A, 25 ml/L stock solution B, 450.9 ml/L stock solution C and spectinomycin added to a concentration of 50 mg/L in sterile ddH$_2$O (stock solution A: K$_2$HPO$_4$ 60.0 g/L, NaH$_2$PO$_4$ 20.0 g/L, adjust pH to 7.0 with KOH and autoclave; stock solution B: NH$_4$Cl 20.0 g/L, MgSO$_4$.7H$_2$O 6.0 g/L, KCl 3.0 g/L, CaCl$_2$ 0.20 g/L, FeSO$_4$.7H$_2$O 50.0 mg/L, autoclave; stock solution C: glucose 5.56 g/L, agar 16.67 g/L and autoclave). Two ways to grow Agrobacterium were used for transformation.

1. Growing Agrobacterium on Solid Medium

A single colony or multiple colonies were picked from the master plate and streaked onto a plate containing PHI-M medium and incubated at 28° C. in the dark for 1-2 days.

Five mL Agrobacterium infection medium and 5 μL of 100 mM 3'-5'-Dimethoxy-4'-hydroxyacetophenone (acetosyringone) were added to a 14 mL Falcon tube in a hood. About 3 full loops of Agrobacterium were suspended in the tube and the tube was then vortexed to make an even suspension. One mL of the suspension was transferred to a spectrophotometer tube and the OD of the suspension was adjusted to 0.35 at 550 nm. The *Agrobacterium* concentration was approximately 0.5×10$^9$ cfu/mL. The final *Agrobacterium* suspension was aliquoted into 2 mL microcentrifuge tubes, each containing 1 mL of the suspension. The suspensions were then used as soon as possible.

2. Growing *Agrobacterium* on Liquid Medium

One day before infection, a 125 mL flask was set up with 30 mLs of 557 A and 30 uL spectinomycin (50 mg/mL) and 30 uL acetosyringone (20 mg/mL). A half loopful of *Agrobacterium* was suspended into the flasks and placed on a 200 rpm shaker at 28° C. overnight. The *Agrobacterium* culture was centrifuged at 5000 rpm for 10 min. The supernatant was removed and the *Agrobacterium* infection medium+acetosyringone solution was added. The bacteria were resuspended by vortex and the OD of *Agrobacterium* suspension was adjusted to 0.35 at 550 nm.

Maize Transformation:

Ears of maize (*Zea mays* L.) cultivars, PHR03 and PH4CN, were surface-sterilized for 15-20 min in 20% (v/v) bleach (5.25% sodium hypochlorite) plus 1 drop of Tween 20 followed by 3 washes in sterile water. Immature embryos (IEs) were isolated from ears and were placed in 2 mL of the *Agrobacterium* infection medium plus acetosyringone solution. The optimal size of the embryos was 1.5-1.8 mm and 1.3-2.1 mm for PHR03 and PH4CN, respectively. The solution was drawn off and 1 mL of *Agrobacterium* suspension was added to the embryos and the tube vortexed for 5-10 sec. The microfuge tube was allowed to stand for 5 min in the hood. The suspension of *Agrobacterium* and embryos were poured onto co-cultivation medium. Any embryos left in the tube were transferred to the plate using a sterile spatula. The *Agrobacterium* suspension was drawn off and the embryos placed axis side down on the media. The plate was sealed with Parafilm tape and incubated in the dark at 21° C. for 1-3 days of co-cultivation.

Embryos were transferred to resting medium without selection. Three to 7 days later, they were transferred to green tissue induction medium containing 3-5 mg/L bialaphos (Meiji Seika K. K., Tokyo, Japan) plus 100 mg/L carbenicillin (ICN, Costa Mesa, Calif.). The plate was sealed with Parafilm and incubated at 26° C.±2° C. under dim light. At 2-3 weeks after the first round selection, each callusing piece, broken into 1 to 3 pieces, depending on initial size, was transferred to fresh medium supplemented with a selective agent. Tissues were subcultured on fresh medium containing bialaphos at 2-3 week intervals. At 3$^{rd}$ round selection, transgenic sectors were identified by visible markers (e.g. RFP) under a fluorescence microscope and chopped into small pieces to place on maintenance medium for further proliferation. Transgenic green tissues were proliferated until sufficient amount of tissues was obtained. Table 1 below shows transgenic events produced from PHR03 and PH4CN using different Bt gene constructs.

TABLE 1

Transgenic maize events transformed with different Bt gene constructs

| Construct | Inbred | Bt gene | #transgenic events/ |
|---|---|---|---|
| PHP26650 | PH4CN | Control | 37 |
|  | PHR03 |  | 44 |
| PHP36779 | PH4CN | Shuffled Bt variant | 12 |
|  | PHR03 | 2A12-V1 | 2 |

TABLE 1-continued

Transgenic maize events transformed with different Bt gene constructs

| Construct | Inbred | Bt gene | #transgenic events/ |
|---|---|---|---|
| PHP36782 | PH4CN | Shuffled Bt variant | 14 |
|  | PHR03 | 2A12-V2 | 38 |
| 34651- Bt Variant V6 | PH4CN | Bt variant V6 | 2 |
|  | PHR03 |  | 169 |
| 34651- Shuffled Bt variant 2A12-V5 | PH4CN | Shuffled Bt variant | 3 |
|  | PHR03 | 2A12-V5 | 86 |
| 34651- Shuffled Bt variant 2A12-V3 | PH4CN | Shuffled Bt variant | — |
|  | PHR03 | 2A12-V3 | 48 |
| 34651- Shuffled Bt variant 2A12-V4 | PH4CN | Shuffled Bt variant | — |
|  | PHR03 | 2A12-V4 | 49 |

Example 3

Continuous Root or Root/Shoot Production from Green Regenerative Tissues of Transgenic Maize Events Highly regenerative, green tissues of monocot crops species contain multiple, light to dark green, shoot meristem-like structures. These tissues regenerate multiple shoots without loss or with minimum loss of regenerability for more than a year. These green tissues are organogenic, rather than embryogenic, and are likely to have meristem-like tissues which are ready for shoot regeneration and root formation. Transgenic sectors were identified by visible markers under a fluorescence microscope and chopped into small pieces to place on maintenance medium for minimal proliferation. Tissues were then transferred directly onto 2 different shoot and root regeneration culturing schemes: (1) 7-14 days of incubation on 289 F shoot regeneration medium prior to placing tissues on rooting medium and (2) directly onto 2 rooting media, MSA and MSB. MSB was more efficient in root formation than MSA. When green tissues were incubated directly on MSB, both shoot and root formation or root formation only was observed. The use of 289 F shoot regeneration medium could facilitate shoot production more efficiently. Transgenic roots could be produced without any shoot regeneration when green tissues with no shoot regeneration on 289 F were transferred onto MSB Regenerated shoot and root tissues showed uniform expression of RFP. This system can be used to do quick gene testing in roots such as corn root worm assay and functionality test of root-specific promoters using stably transformed tissues.

Example 4

Screening of Transgenic Maize Events with Bt Gene Expression by Western Blot Analysis In order to screen transgenic events with Bt gene expression, western blot hybridization analysis was carried out. Forty to 100 mg of green tissues or leaf or root tissues from each transgenic event were mixed with 0.1 to 0.25 mL CCLR protein extraction buffer (100 mM phosphate buffer, 1 mM EDTA, 1% Triton, 10% Glycerol, 7 mM BME, pH 7.8) (Cat. #E1531, Promega Corp., Madison, Wis.) in a 2 mL microfuge tube. After adding two steel balls in the tube, the samples were ground two to three times with the GenoGrinder2000 (1× rate, 2 min 30 sec/run; 250 strokes/min). After centrifugation (10,000×g for 2 min), 30 μL of the supernatant and 10 μL of 4× loading dye were mixed in a fresh tube and heated for 5 min at 95° C. Twenty μL of total soluble protein (total 6000 μg wet tissue equivalent) from each event and purified Bt protein as a positive control were separated on SDS-PAGE using NuPAGE 4-12% Bis Tris gel (Invitrogen Corp, Carlsbad, Calif.) and transferred to nitrocellulose membrane. After transfer, the membrane was blocked in TBS-T (10 mM Tris-HCl, pH 8.0, 150 mM NaCl, 0.1% Tween 20)+5% nonfat dried milk overnight. After washing (2×5 min) in TBS-T, primary rabbit polyclonal Bt antibody was added at 1:1000 dilution and incubated for 1.5 to 2 hr at room temperature. After washing in 1% BSA/TBS-T, the membrane was incubated in goat anti-rabbit alkaline phosphatase (AP) antibody at 1:1000 dilution for 1-2 hr at room temperature and washed as indicated above. Labeling was monitored by using Bio-Rad (Hercules, Calif.) AP conjugate substrate kit for detection according to manufacturer's instructions. Expression signal was quantified using UN-SCAN-IT gel (Gel & Graph Digitizing Software 6.1, Silk Scientific, Inc., Orem, Utah).

Bt expression in transgenic events was determined by western analysis using green tissues and leaf and root tissues from each event. Out of 6 Bt variants, shuffled Bt variant 2A12-V5 had the highest expression of Bt (60 ppm) in green tissues while shuffled Bt variant 2A12-V2 was lowest in expression (7 ppm). Shuffled Bt variants 2A12-V1, 2A12-V3, 2A12-V4, and 2A12-V6 showed 26, 36, 28 and 38 ppm, respectively. In general, root and leaf tissues had much lower levels of Bt expression, compared with that of green tissues derived from the same event, e.g., root (7 ppm) and leaf tissues (6 ppm) vs. green tissues (23 ppm) from shuffled Bt variant 2A12-V4 event #2. For each construct 3 to 8 highest expressors were selected for shoot and/or root regeneration for Western corn rootworm (WCRW) bioassay.

Example 5

Establishment and Optimization of a Contamination-Free In Vitro Insect Bioassay System Using Live Plantlets or Root Tissues Preparation of Plantlets or Root Tissues:

Plantlets used for western corn rootworm bioassay were selected from high expression events containing Bt genes. Plantlet selections were based on root thickness and root mass, preferably with a single shoot and either thin young roots or highly branched young roots. A mixture of MSA with 0, 1, 1.5, 2 and 5% Plant Preservative Mixture (PPM—0.1350% 5-chloro-2methyl-3(2H)-isothiazolone, 0.0412% 2-methly-3(2H)-isothiasolone, 99.8238% inert ingredients, Plant Cell Biotechnology, Inc.) was prepared for plantlet soak and as a nutrient solution. Two mL MSA-PPM mixture on two 70 mm circular Whatman (Schleicher & Schuell) filter papers in Petri dishes (100×15 mm, VWR) were set-up for plantlet/root containment. Individual plantlets were extracted from MSB media and roots were removed from agar by forceps. Extraneous yellow and browning tissue, leaves and roots were cut away or excised. Each plantlet was soaked in 50 mL MSA containing different levels of PPM for 3 to 5 minutes. After soaking, stray residual agar and extra nutrient solution were removed from each plantlet, and the roots then arranged for maximum contact with the filter paper within the prepared Petri dishes, one plantlet per Petri dish. Plant materials were submitted for 1 day old WCRW infestation Root tissues alone without leaves also could be prepared for the assay using the same protocol described above.

Preparation of Western Corn Root Worms:

Non-diapausing WCRW eggs were cleaned and surface sterilized in successive steps using a modification of the procedure described by Marrone et al. (1985) (J of Economic Entomology 78: 290-293), with 1% Clorox bleach, 0.25% peracetic acid solution, 70% ethanol, and then de-ionized water. The final step utilizes washing with deionized water four times. Eggs were suspended in a 0.22% agarose solution and transferred to agar Petri plates covered with two 9 cm filter paper disks. Once dry, the eggs were sprayed with a thin layer of Professional Lysol Disinfectant Spray (28.1% a.i.). After they were dry, the plates were covered and four dishes were placed in 32 ounce Nalgene containers that had been sprayed with Lysol, wiped down, and allowed to dry. The Nalgene containers were closed and put in incubators kept at 28° C. in the dark for two days until egg hatch. Neonates were transferred to single-well plates with artificial WCRW diet, sealed with heat-sealable Mylar with pin holes, and kept at 25° C. in the dark for 24 hr.

Infestation of Plantlets with Western Corn Root Worms:

Under a laminar flow hood, larvae were tapped into a heat-sterilized #80 sieve. Larvae were sprayed with or without Professional Lysol Disinfectant Spray (28.10% a.i.) and allowed to soak for 2 min. The larvae were then washed with autoclaved water and transferred to a 50 mL centrifuge tube. Additional autoclaved water was added to the tube and the larvae swirled for 1 minute. The water was decanted, leaving the larvae and a small amount of water in the bottom of the tube. A sterile disposable inoculating loop was used to transfer ~25 larvae to the Petri dishes containing the plantlet. The Petri dish/plantlet/larvae are placed in an incubator at 25° C. in a 16-hr light phase for 5-7 days prior to checking contamination of the plates and plants.

No fungal or bacterial contamination was observed in the plates with MSA solution plus 5% PPM when non-sterilized rootworms were infested (Table 2). In contrast, fungal contamination was detected with 1% or 2% PPM; the higher the level of PPM, the less the contamination. Rootworms, however, were severely stunted at 5% PPM.

TABLE 2

Number of contaminated plates treated with non-sterilized WCRWs at different PPM concentrations in liquid MSA medium. The MSA-PPM mixtures on 2 Whatman filter papers in Petri dishes were set for plantlet/root containment.

| PPM level | 0% PPM | 1% PPM | 2% PPM | 5% PPM |
|---|---|---|---|---|
| # plates contaminated/# plates tested | 2/2 (severe mold contamination) | 1/2 (severe mold contamination) | 1/2 (minor mold contamination) | 0/2 (No mold) |

Another set of experiments was conducted with rootworms sterilized with Lysol. Fungal contamination was controlled in the plates with both 1% and 1.5% PPM treatments (Table 3), but mild bacterial contamination was occasionally observed at 1% PPM. When sterilized rootworms were placed onto agar medium, severe bacterial contamination was detected (data not shown). Based on these results, a filter paper system supplemented with MSA liquid medium containing 1.5% PPM was employed using rootworms sterilized with Lysol for further WCRW bioassay.

TABLE 3

Number of contaminated plates treated with sterilized WCRWs

|  | 1% PPM | 1.5% PPM |
|---|---|---|
| Non-sterilized rootworm | 1/2 (severe mold contamination) | 1/2 (minor mold contamination) |
| Sterilized Rootworm w/Lysol | 0/2 (No Contamination) | 0/2 (No Contamination) |

Example 6

Western Corn Rootworm Bioassay Using Transgenic Maize Events Expressing Bt Genes Transgenic plant materials were produced as described in Example 1-3. Plantlets/root tissues were prepared as described in Example 3. One to 3 plantlets per event were extracted from MSB media and roots were removed of agar by forceps. After soaking in MSA containing 1.5% PPM, stray residual agar and extra nutrient solution were removed from each plantlet, and the roots were then arranged for maximum contact with 3 filter papers within the prepared Sigma Phytatrays, one plantlet per Phytatray vessel. Roots not in contact with the filter paper were weighed down by single 2"×2" stainless steel mesh screens until it was accessible to the nutrient solution. About 20 plantlets were prepared for WCRW bioassay, as well as 1 to 3 control plantlets per inbred line, and used for WCRW infestation.

Under a laminar flow hood, the one-day-old larvae were transferred to a heat-sterilized #80 sieve and sprayed until drenched with Professional Lysol Disinfectant Spray and allowed to soak for 2 min. The larvae were then washed with autoclaved water and transferred to a 50 mL centrifuge tube and swirled for 1 min. The water was decanted, leaving the larvae in a small amount of water in the bottom of the tube. A sterile disposable inoculating loop was used to transfer ~25 larvae to the Phytatray containing the transformed plantlet. After infestation, the Phytatrays were then placed in an incubator at 25° C. in a 16-hr light phase for 7 days prior to scoring the plants and larvae for plant damage and larval development.

As shown, 24 to 36% of larvae developed to the $2^{nd}$ instars (Table 4) and root tissues had severe damage on control plantlets of both PH4CN and PHR03 1 wk after infestation while the growth of rootworms was severely stunted and little root damage was detected on Herculex® plantlets (Table 4). Herculex® RW contains Cry 34/Cry35 toxins. (Pioneer and Dow Agro). The expression level of 6 Bt variants was 7 to 60 ppm in green tissue. In general the higher the Bt expression of the same Bt variant in green tissue, the more resistant the plantlets and roots to rootworms (data not shown). A few events with high Bt expression in green tissue were susceptible to rootworms; these events did not show Bt expression in roots possibly due to production of multiple events derived from the same embryo or transgene silencing as tissue reaches stages of plantlets or roots. All Bt variants tested, except variant 2A12-V2, were slightly to moderately resistant to rootworms. (Table 4). Event #3 transformed with Bt variant V6 (at 21 ppm) had little root damage and stunted root worms 4 days after infestation (data not shown). Event #23 transformed with shuffled variant 2A12-V3 (at 9 ppm) had severe root damage and bigger root worms 4 days after infestation. (data not shown). Event #23 transformed with variant 2A12-V3 (Table 4) and 3 events (#s 3, 5 and 7) with variant 2A12-V2 were low in efficacy, possibly due to low expression (Table 4). The number of the $2^{nd}$ instars and root damage appeared to be the best indicators to evaluate the efficacy of Bt genes and transgenic events (Table 4).

TABLE 4

WCRW bioassay results using $T_0$ PH4CN and PHR03 plantlets

| Expt | Inbred | Construct | Event # | | Rep | # II instars | Crown Damage | Root Damage | Leaf Damage | Plant |
|---|---|---|---|---|---|---|---|---|---|---|
| | | | | Bt expression in tissue, ppm | | | | | | |
| #1 | PH4CN | 26650 (−control) | 6 | 0 | #1 | 6 | ++ | ++ | none | live |
| | | Shuffled | 5 | 12 | #1 | 2 | + | + | none | live |
| | | Bt variant 2A12-V1 | 11 | 12 | #1 | 2 | none | + | none | live |
| | | Shuffled | 3 | 7 | #1 | 4 | ++ | ++ | none | live |
| | | Bt variant 2A12-V2 | 5 | 6 | #1 | 5 | +++ | ++ | none | live |
| | | | 7 | 5 | #1 | 8 | +++ | +++ | none | live |
| | Herculex® RW | (+control) | | n.a. | #1 | 0 | none | (+) | none | live |
| | | | | Bt expression in GT, ppm | | | | | | |
| #2 | PHR03 | 26650 (−control) | 6 | 0 | #1 | 9 | +++ | +++ | some | dying |
| | | | | 0 | #2 | 6 | +++ | +++ | moderate | dead |
| | | Shuffled | 22 | 27 | #1 | 3 | + | ++ | none | healthy |
| | | Bt variant 2A12-V3 | | 27 | #2 | 1 | + | ++ | some | dying |
| | | | 23 | 9 | #1 | 12 | +++ | +++ | some | dying |

TABLE 4-continued

WCRW bioassay results using $T_0$ PH4CN and PHR03 plantlets

| Expt | Inbred | Construct | Event # | | Rep | # II instars | Crown Damage | Root Damage | Leaf Damage | Plant |
|---|---|---|---|---|---|---|---|---|---|---|
| | | Shuffled Bt variant 2A12-V6 | 3 | 21 | #1 | 0 | none | + | none | dying |
| | | | | 21 | #2 | 0 | + | ++ | none | dying |
| | | | | 21 | #3 | 0 | none | none | none | healthy |
| | | | 10 | 23 | #1 | 7 | ++ | ++ | some | dying |
| | | | | 23 | #2 | 0 | ++ | + | none | healthy |
| | Herculex ® RW | (+control) | | n.a. | #1 | 0 | none | + | some | healthy |

Example 7

Application of the Current WCRW Bioassay System to Other Insects

This example illustrates significant pest inhibition obtained by feeding lepidopteran larvae on corn tissue transformed with Bt genes.

Corn earworm, fall armyworm, black cutworm and sugarcane borer eggs were received from Benzon Research (Carlisle, Pa.). European corn borer eggs were received from Pioneer (Johnston, Iowa). Soybean looper eggs were received from DuPont (Wilmington Experiment Station, Del.). Eggs were kept at 28° C. and allowed to hatch. Neonates were placed on a multi-species lepidopteran diet (Southland Products, Lake Village, Ak.) and kept at 28° C. for 24 hr. Under a laminar flow hood, 10 one-day-old larvae were transferred to the Phytatray containing the transgenic plantlet using a sterile disposable inoculating loop. Prior to infestation, a minimal amount of plant nutrients and 1.5% PPM was applied to the 3 sterile filter papers on which the plantlet was placed, as described in Examples 4, 5 and 6. Metal mesh screen was placed on the roots of the plantlet to insure good contact between the roots and the plant nutrients on the filter paper if necessary. The Phytatrays were then placed in an incubator at 26° C. in a 16-hr light phase for 3-7 days prior to scoring the plants and larvae for plant damage and larval development. Plants were observed to determine those expressing Bt to kill or stunt the lepidopteran pests compared to the control which were not expressing toxin.

Table 5 demonstrates the effect of Bt 1 expression in corn plantlets on resistance to soybean looper. All transgenic events (#s 2, 16, 17, and 33) showing the Bt1 gene presence had good resistance to soybean looper while negative control (#583) and Herculex®RW without Bt1 were susceptible to soybean looper (Table 5)

TABLE 5

In vitro soybean looper bioassay results using $T_0$ PHR03 plantlets

| Construct (event #) | Bt1 gene presence | Insect # alive | Insect # dead | Condition of leaves (0% to 100%) | Condition of insects |
|---|---|---|---|---|---|
| 24600 (#583) | − | 20 | 0 | 50% eaten | Several third instars |
| Bt1 (#40) | − | 7 | 13 | 20% eaten | All seven still 1st instars (stunted) |
| Bt1 (#33) | + | 0 | 20 | 0% eaten | All dead neonates |
| Bt1 (#17) | + | 0 | 20 | 0% eaten | All dead neonates |
| Bt1 (#16) | + | 0 | 20 | 0% eaten | All dead neonates |
| Bt1 (#2) | + | 0 | 20 | 2% eaten, slight holes in leaves | All dead neonates |
| Herculex ®RW | − | 14 | 6 | 80% eaten | Various instars up to 3rds |

Twenty neonates of soybean looper were infested onto corn plantlets. Five days after infestation plant damage and insect growth, stunting and survival were scored.

Table 6 demonstrates the effect of Bt 1 expression in corn plantlets on resistance to black cutworm. Transgenic event #54 showing the Bt1 gene presence had good resistance to black cutworm while event #40 without Bt1 was susceptible to black cutworm.

TABLE 6

In vitro black cutworm bioassay results using $T_0$ PHR03 plantlets

| | Bt1 gene presence | Insect # alive | Insect # dead | Leaf damage | Plant health |
|---|---|---|---|---|---|
| Bt1 (#54) | + | 3 | 7 | 10%, stem & leaves pocked | Alive |
| Bt1 (#40) | − | 10 | 0 | 95%, stem completely shredded, everything eaten | Dead |

TABLE 6-continued

In vitro black cutworm bioassay results using T₀ PHR03 plantlets

| | Bt1 gene presence | Insect # alive | Insect # dead | Leaf damage | Plant health |
|---|---|---|---|---|---|
| Herculex ®RW | – | 5 | 5 | 80%, stem shredded; leaves shredded | Dead |

Ten neonates of black cutworm were infested onto corn plantlets. Seven days after infestation plant damage and insect growth, stunting and survival were scored.

Table 7 demonstrates the effect of Bt 1 expression in corn plantlets on resistance to corn earworm. Transgenic event #s 25, 42 and 82 showing the Bt1 gene presence had good resistance to corn earworm while event #40 and Herculex®RW without Bt1 were susceptible to corn earworm.

TABLE 7

In vitro corn earworm bioassay results using T₀ PHR03 plantlets

| | Bt1 gene presence | Insect # alive | Insect # dead | Leaf damage | Plant health |
|---|---|---|---|---|---|
| Bt1 (#42) | + | 0 | 10 | 0%, no penetration | Healthy |
| Bt1 (#82) | + | 0 | 10 | 0%, no penetration | Healthy |
| Bt1 (#25) | + | 0 | 10 | 0%, one penetration hole, but did not go anywhere | Healthy |
| Bt1 (#40) | – | 10 | 0 | 95%, stem completely shredded, everything eaten | Dead |
| Herculex ®RW | – | 5 | 5 | 80%, stem shredded; leaves shredded | Dead |

Ten neonates of corn earworm were infested onto corn plantlets. Seven days after infestation plant damage and insect growth, stunting and survival were scored.

Table 8 demonstrates the effect of Bt 1 expression in corn plantlets on resistance to fall armyworm and sugarcane borer. All transgenic events except event #20 showing the Bt1 gene presence had good resistance to both fall armyworm and sugarcane borer while negative control (#5) and Herculex®RW without Bt1 were susceptible to these two lepidopteras (Table 8). All events were consistent in tolerance to both fall armyworm and sugarcane (Table 8). Transgenic event #20 was susceptible to both lepidopteras possibly due to lack of Bt1 expression even with the presence of Bt1 gene.

TABLE 8

In vitro fall armyworm and sugarcane borer bioassay results using T₀ PHR03 plantlets

| Insect | Construct event # | Bt1 gene presence | Insect # alive | Insect # dead | Condition of leaves (0% to 100%) | Condition of insects |
|---|---|---|---|---|---|---|
| Fall armyworm | 26500 (#5) | – | 14 | 1 | 70% eaten | Survivors premolt to III |
| | Bt1 (#8) | + | 0 | 15 | 2% eaten | All dead neonates |
| | Bt1 (#51) | + | 0 | 15 | 4% eaten | All dead neonates |
| | Bt1 (#12) | + | 4 | 11 | 8% eaten | Survivors still Ists |
| | Bt1 (#20) | + | 11 | 4 | 65% eaten | Survivors premolt to III |
| | Herculex ®RW | – | 13 | 2 | 85% eaten | Survivors premolt to III |

| Insect | Construct event # | Bt1 gene presence | Stalk holes | Condition of leaves (0% to 100%) | |
|---|---|---|---|---|---|
| Sugarcane borer | 26650 (#5) | – | 10 | Plant dead, stalk collapsed | |
| | Bt1 (#8) | + | 2 | Plant healthy | |
| | Bt1 (#51) | + | 6 | Plant alive | |
| | Bt1 (#12) | + | 6 | Plant dying | |
| | Bt1 (#20) | + | 8 | Plant dying, stalk collapsed | |
| | Herculex ®RW | – | ? | Plant dead, stalk completely collapsed unable to count | |

*Some feeding on leaves, but neonates of sugarcane borer borrowed into stalks within an hour and survivors could not be scored live/dead/.

Example 8

In Vitro Bioassay Using Multiple Insects

This innovative in vitro bioassay using plantlets provides a novel method to analyze effectiveness of gene constructs using both damages to the plant as well as development of insect. Until recently, we have only performed this bioassay using one insect at a time; however, a multiple insect test has been successfully implemented in this example. To prepare plantlets for this system, the whole plantlet was carefully extracted from the MSB rooting medium with roots intact and with as much agar off roots as possible and soaked for 5 minutes in a MSA+1.5% PPM solution. A wire grid might be used to weigh down the plantlet in the solution. After 5 min, the plantlet was carefully taken out and placed in a phytatray container containing 3 pieces of filter paper with 3 mL of MSA+1.5% PPM solution. The roots were spread out and the root/leaf was cut down if necessary so that all plantlets were equivalent. If only using one type of insect for infestation, the plantlets were infested and scored according to protocol about one week later. Multiple insects could also be used. If the feeding source of the insects was different, i.e. one type fed on roots whereas the other fed on leaves, they could be infested together on the same day. When using multiple insects, they could also be infested separately depending on how soon results showed, i.e. leaf-eating insect (lepidoptera) on one day and root-eating insect three days later.

Table 9 demonstrates in vitro bioassay results using multiple insects in $T_0$ quality event corn plantlets; all quality events contain Bt1 gene for lepidopteran resistance and Bt2 and Bt3 genes for rootworm resistance. All transgenic events showed resistance to both FAW and WCRW while negative control plantlets were susceptible to both insects (Table 9). Infestation of both FAW and WCRW together was very efficient in screening of transgenic events resistant to both insects compared with infestation of each insect separately. The surviving plantlets were transplanted to soil for additional insect bioassay, further molecular assay and grown to maturity to harvest seed. This bioassay scheme provides an efficient and time-saving pre-screening system for transgenic events (FIG. 1).

TABLE 9

In vitro bioassay using multiple insects in $T_0$ PHR03 plantlets

| Insect treatment | Construct (event #) | Condition of leaves | Condition of insects |
|---|---|---|---|
| WCRW + FAW* | - control (#623) | plant dead; entire stalk and roots destroyed (unclear if FAW ate roots as well) | 5 FAW alive (III instars), no WCRW found |
| | QE #8 | no stalk damage - healthy plant; tiny pinhole damage (very slight), no root damage | no live FAW, no growth of WCRW |
| | QE #76 | no stalk damage - healthy plant; 5% damage to leaves by FAW, small damage to roots | 2 FAW alive (II instars), WCRW alive but stunted |
| FAW-> WCRW** | - control (#623) | plant dying; stalk damage, 50% leaf eaten, no roots eaten by FAW | 8 FAW alive (III instars), one rootworm visible |
| | QE #8 | healthy plant; no leaf damage | no live FAW, WCRW not on roots (repellency?) |
| | QE #76 | healthy plant; no leaf damage | no live FAW, WCRW on roots but stunted |
| FAW-> WCRW* | - control (#623) | plant dead; nothing left | 4 FAW alive (III instars) |
| | QE #76 | healthy plant; 5% leaf damage from FAW, no root damage yet | 1 FAW (I), little WCRW mortality |
| | QE #105 | plant collapsing, browning; 10% leaf damage, minor root damage | 3 FAW (II), some WCRW mortality |
| | QE #119 | plant alive, green; 15% leaf damage, no root damage | 3 FAW (II), no WCRW mortality |
| FAW + WCRW** | - control (#623) | plant dead; stalk left, no roots, 70% leaf damage | 3 FAW (III) +' 1 eaten, 1 WCRW |
| | QE #76 | healthy plant; no leaf damage, some root damage | 0 FAW, some WCRW mortality |
| | QE #105 | alive but collapsed; 20% leaf damage, no root damage | 4 FAW (II), some WCRW mortality |
| | QE #119 | plant alive; 30% leaf damage, no root damage | 2 FAW (II), ~50% WCRW mortality |

TABLE 9-continued

In vitro bioassay using multiple insects in T₀ PHR03 plantlets

| Insect treatment | Construct (event #) | Condition of leaves | Condition of insects |
|---|---|---|---|
| WCRW->FAW*** | - control (#623) | plant dead; stalk only left, major root damage, 70% leaf damage | 6 FAW (3 III, 3 II), 3 WCRW (II) |
| | QE #76 | Alive; 20% leaf damage, minor root feeding | 3 FAW (I), 0 WCRW |
| | QE #105 | alive but collapsed; 5% leaf damage, no root damage | 6 FAW (I), 0 WCRW |
| | QE #119 | plant alive; pinhole leaf damage, no root damage | 2 FAW (I), 70% WCRW mortality |

*Both 25 neonates of western corn rootworm (WCRW) and 10 neonates of fall armyworm (FAW) were infested together at the same time.
**10 neonates of FAW were infested first and 4 days later 25 neonates of WCRW were infested.
***25 neonates of WCRW were infested first and 6 days later 10 neonates of FAW were infested.

Example 9

In Vitro Insect Bioassay for Promoter Testing

This example illustrates the application of the in vitro lepidopteran insect bioassay system to test different promoters do drive the expression of the Bt gene. Two constructs were used for corn transformation: one containing Bt1 driven by the maize ubiquitin promoter (Ubi1-Bt1) and another driven by the banana streak virus promoter (BSV TR-Bt1). Plantlets were regenerated from transgenic events and leaf punches were harvested for copy # assay by qPCR. Single copy events were used for in vitro insect bioassay.

Under a laminar flow hood, 10 one-day-old larvae of fall armyworm (FAW) were transferred to the Phytatray containing the transgenic plantlet using a sterile disposable inoculating loop. Prior to infestation, a minimal amount of plant nutrients and 1.5% PPM was applied to the 3 sterile filter papers on which the plantlet was placed. Metal mesh screen was placed on the roots of the plantlet to insure good contact between the roots and the plant nutrients on the filter paper if necessary. The Phytatrays were then placed in an incubator at 26° C. in a 16-hr light phase for 3-7 days prior to scoring the plants and larvae for plant damage and larval development. Plants were observed to determine those expressing Bt to kill or stunt FAW compared to the control which were not expressing toxin.

Table 10 demonstrates the effect of Bt 1 expression driven by 2 different promoters in corn plantlets on resistance to FAW. All transgenic events showed good resistance to fall armyworm, but the degree of insect resistance was higher with the maize ubiquitin promoter than banana streak virus promoter (Table 10). Bt1 expression of each event will be measured by ELISA or western blot analysis.

Example 10

In Vitro Insect Bioassay Using Transgenic Green Regenerative Tissue Events

Our green tissue bioassay system also can provide a method for pre-screening of genes/promoters. The process is similar to the in vitro bioassay system that was described in Example 5, but instead of using maize plantlets, green regenerative tissues were used. Using all sterile materials, two pieces of filter paper were placed into a Petri dish and about 1.5 mL of MSA+1.5% PPM solution were pipetted onto the filter paper. If there was excess solution, or not enough solution, solution was removed/added until the filter papers were evenly soaked but not dripping. Five good pieces of green tissue were selected and placed onto the filter paper; good callus tissue is defined as a piece about 5 mm, and regenerable, compact, and green. Also, for all events being screened, there should be the same amount of green tissues and they should all be equivalent in quality and size. The Petri dish was infested with the insect which the gene that was being tested was resistant against and the plate was sealed with parafilm to prevent contamination. Two days after infestation, additional solution was added to keep the tissue healthy. After 6 to 12 days, tissue damage and insect growth/stunting/death were scored per scoring protocol.

Transgenic maize green tissue events transformed with 4 different shuffled Bt variants were tested for WCRW resistance. As expected, negative control events were susceptible to WCRW and tissues became brown and some neonates grew

TABLE 10

Promoter test in T₀ PHR03 plantlets using in vitro insect bioassay

| Promoter | Construct event # | Condition of leaves (0% to 100%) | Condition of insects |
|---|---|---|---|
| -Control | 26500 (#5) | 70-100% eaten | Survivors premolt to III |
| Maize ubiquitin | UbiI-Bt1 (#8) | 0% eaten | All dead neonates |
| | UbiI-Bt1 (#12) | 5% pinhole damage | All dead neonates |
| | UbiI-Bt1 (#18) | 2% eaten | All dead neonates |
| | UbiI-Bt1 (#47) | 0% eaten | All dead neonates |
| | UbiI-Bt1 (#51) | 4% eaten | All dead neonates |
| Banana streak virus | BSV TR-Bt1 (#12) | 8% eaten | Survivors still 1sts |
| | BSV TR-Bt1 (#76) | 5% eaten | Survivors still 1sts |
| | BSV TR-Bt1 (#82) | 0% eaten, stalk damage | All dead neonates |
| | BSV TR-Bt1 (#105) | 10% eaten | 3 survivors to II |
| | BSV TR-Bt1 (#116) | Pinhole damage | All dead neonates |
| | BSV TR-Bt1 (#119) | 15% eaten | 3 survivors to II | to the healthy $2^{nd}$ instars (Table 11). Event #s 48 and 50 transformed with the shuffled Bt variant 14 showed good efficacy to rootworms while event #95 transformed with the shuffled Bt variant 1, event #36 transformed with the shuffled Bt variant 2 and event #10 with the shuffled Bt variant 3 showed slightly to moderately resistant to rootworms. Clearer results could be obtained when the tissues were maintained for longer than 2 weeks. Thus, this green tissue bioassay system can be used for early screening of transgenic events.

TABLE 11

WCRW bioassay using $T_0$ PHR03 green regenerative tissues

| Construct | Event # | Tissue Damage | Insect growth/healthiness |
|---|---|---|---|
| 24600 (- control) | 6 | +++, brown | healthy |
| 26650 (- control) | 1 | +++, brown | healthy |
| Shuffled Bt variant 1 | 34 | ++(+), brown | healthy |
|  | 59 | +++, brown | healthy |
|  | 95 | +, most of them green | several dead/stunted |
| Shuffled Bt variant 2 | 36 | +(+), most of them green | several stunted |
| Shuffled Bt variant 3 | 9 | ++(+), brown | healthy |
|  | 10 | +(+), some green | some stunting |
| Shuffled Bt variant 14 | 4 | ++(+), brown | healthy |
|  | 48 | 0, green | mortality and stunting |
|  | 50 | (+), green | mortality but some healthy |

Tissue damage and insect growth/stunting/death were scored 6 days after WCRW infestation.

Example 11

In Vitro Bioassay Using Different Explants for Insect Infestation

Different types of tissue were used for in vitro insect bioassay following the similar sterilization and culture protocol used for the in vitro insect bioassay protocol described above. Roots, leaves, callus- and green tissue-derived plantlets, and mature seed- and immature embryo-derived seedlings were used as target explants for insect infestation. Plantlets and germinating seedlings were, in general, best for in vitro insect bioassay using both rootworms and lepidopteras (Table 12).

TABLE 12

In vitro insect bioassay efficiency using different in vitro-derived tissue types

| Tissue type Insect | Root | Leaf | Green regenerative tissue | Callus | Regenerated plantlet w/ root | Germinating seedling from mature seed w/ root | Germinating seedling from immature seed w/ root |
|---|---|---|---|---|---|---|---|
| Rootworm | +++ | + | ++(+) | n.t. | +++ | +++ | +++ |
| *Lepidoptera* | ++ | +++ | +++ | n.t. | +++ | +++ | +++ |

*n.t.: not tested

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

That which is claimed:

1. A bioassay method comprising:
 a) contacting a transgenic sterilized maize plant tissue comprising a *Bacillus thuringiensis* (Bt) gene in a culture dish under sterile conditions with a culturing medium, the culturing medium comprising a biocide that inhibits fungal and bacterial growth, and a substantially sterile absorbent material wherein the substantially sterile absorbent material is in contact with the sterilized maize plant tissue and the culturing medium;
 b) providing a sterilized insect pest; and
 c) determining a phenotype of the plant tissue exposed to the pest; wherein the method has minimal or no fungal or bacterial contamination;
 wherein the phenotype is selected from the group consisting of crown damage, root damage, leaf damage, leaf wilting, change in leaf color, change in root color, change in stem color, and plant death.

2. The bioassay method of claim 1, wherein the sterilized maize plant tissue is selected from the group consisting of callus tissue, green tissue, meristematic tissue, and at least one live root of a plantlet.

3. The bioassay method of claim 2, wherein the plantlet further comprises a plurality of roots.

4. The bioassay method of claim 2, further comprising providing a plurality of plantlets regenerated from the sterilized maize plant tissue selected from the group consisting of, callus tissue, green tissue, and meristematic tissue.

5. The bioassay method of claim 1, wherein the pest is selected from the group consisting of the order of Lepidoptera, Homoptera, Heteroptera, and Coleoptera.

6. The bioassay method of claim 1, wherein the pest is of a developmental stage selected from the group consisting of an egg, a larva, an instar, and an adult.

7. The bioassay method of claim 2, wherein the root is transgenic for a Bt gene, and wherein the pest is western corn rootworm (WCRW).

8. The bioassay method of claim 1, wherein the sterilized maize plant tissue further comprises a phenotype selected from the group consisting of tolerance to a biotic stress, tolerance to a pest, resistance to a pest, tolerance to a pathogen, resistance to a pathogen, increased disease resistance, and a nutritional enhancement.

9. The bioassay method of claim 5, wherein the pest is selected from the group consisting of Western corn rootworm (WCRW), corn earworm, fall armyworm (FAW), black cutworm, sugarcane borer, European corn borer (ECB), and soybean looper.

10. The bioassay method of claim 1, further comprising determining the phenotype of the insect pest.

11. The bioassay method of claim 10, wherein the phenotype of the insect pest is selected from the group consisting of live, dead, stunted, and instar stage.

* * * * *